(12) United States Patent
Park (10) Patent No.: US 7,598,488 B2
(45) Date of Patent: Oct. 6, 2009

(54) APPARATUS AND METHOD FOR FIELD ASYMMETRIC ION MOBILITY SPECTROMETRY COMBINED WITH MASS SPECTROMETRY

(76) Inventor: Melvin A. Park, 8 Hardwood Dr., Billerica, MA (US) 01821

(*) Notice: Subject to any disclaimer, the term of this patent is extended or adjusted under 35 U.S.C. 154(b) by 387 days.

(21) Appl. No.: 11/533,515

(22) Filed: Sep. 20, 2006

(65) Prior Publication Data

US 2008/0067367 A1 Mar. 20, 2008

(51) Int. Cl.
*B01D 59/44* (2006.01)
(52) U.S. Cl. .................. 250/290; 250/282; 250/288; 250/286
(58) Field of Classification Search .......... 250/281, 250/290, 288, 287, 282, 286
See application file for complete search history.

(56) References Cited

U.S. PATENT DOCUMENTS

| | | | |
|---|---|---|---|
| 4,542,293 A | 9/1985 | Fenn et al. | |
| 5,420,424 A | 5/1995 | Carnahan et al. | |
| 5,844,237 A | 12/1998 | Whitehouse et al. | |
| 5,905,258 A | 5/1999 | Clemmer et al. | |
| 6,323,482 B1 | 11/2001 | Clemmer et al. | |
| 6,498,342 B1 | 12/2002 | Clemmer | |
| 6,504,149 B2 | 1/2003 | Guevremont | |
| 6,559,441 B2 | 5/2003 | Clemmer | |
| 6,777,672 B1* | 8/2004 | Park | 250/288 |
| 6,960,761 B2 | 11/2005 | Clemmer | |
| 6,972,407 B2 | 12/2005 | Miller et al. | |
| 7,077,944 B2 | 7/2006 | Clemmer | |
| 7,098,449 B1* | 8/2006 | Miller et al. | 250/287 |
| 7,109,478 B2* | 9/2006 | Park | 250/288 |
| 7,265,349 B2* | 9/2007 | Park | 250/288 |
| 2002/0134932 A1* | 9/2002 | Guevremont et al. | 250/281 |
| 2002/0168268 A1* | 11/2002 | Lin et al. | 417/76 |
| 2005/0006578 A1* | 1/2005 | Rockwood et al. | 250/289 |
| 2005/0258360 A1* | 11/2005 | Whitehouse et al. | 250/288 |
| 2006/0163471 A1* | 7/2006 | Zapata et al. | 250/288 |
| 2006/0186333 A1* | 8/2006 | Hill et al. | 250/288 |

OTHER PUBLICATIONS

International Search Report dated Apr. 8, 2008 for priority PCT application No. PCT/US2007/078695.
Barnett, et al., "Application of ESI-FAIMS-MS to the Analysis of Tryptic Peptides", Journal of the American Society of Mass Spectrometry, 2002, pp. 1282-1291, vol. 13, Elsevier Science Inc., Ontario, Canada.
Buryakov, et al., "A New Method of Separation of Multi-Atomic Ions by Mobility at Atmospheric Pressure Using a High-Frequency Amplitude-Assymetric Strong Electric Field", International Journal of Mass Spectrometry and Ion Processes, 1993, pp. 143-148, vol. 128, Elsevier Science Publishers B.V.

(Continued)

*Primary Examiner*—Nikita Wells
*Assistant Examiner*—Johnnie L Smith
(74) *Attorney, Agent, or Firm*—Law Office of Paul E. Kudirka (57) ABSTRACT

In a system for analyzing samples by mass spectrometry, analyte ions are analyzed first by field asymmetric ion mobility spectrometry (FAIMS) before being analyzed by a mass analyzer. The analyte ions are produced in an ion source operating at near atmospheric pressure and transferred via a dielectric capillary into the vacuum system of the mass analyzer. While passing through the capillary, the ions are analyzed by FAIMS via electrodes on the interior wall of the capillary.

21 Claims, 9 Drawing Sheets

OTHER PUBLICATIONS

Ells, et al., "Detection of Chlorinated and Brominated Byproducts of Drinking Water Disinfection Using Electrospray Ionization—High-Field Asymmetric Waveform ion Mobility Spectrometry—Mass Spectrometry", Analytical Chemistry, Oct. 15, 1999, pp. 4747-4752, vol. 71, No. 20.

Gabryelski, et al., "Rapid and Sensitive Differentiation of Anomers, Linkage, and Position Isomers of Disaccharides Using High-Field Asymmetric Waveform Ion Mobility Spectrometry (FAIMS)", Journal of American Society for Mass Spectrometry, 2003, pp. 265-277, vol. 14, Elsevier Science, Inc.

Guevremont, et al., "Comparison of Experimental and Calculated Peak Shapes for Three Cylindrical Geometry FAIMS Prototypes of Differing Electrode Diameters", Journal of American Society for Mass Spectrometry, 2004, pp. 349-362, vol. 16, Elsevier, Inc.

Reigner, et al., "Qualitative Evaluation of Field Ion Spectrometry for Chemical Warfare Agent Detection", Proceedings of the 45th ASMS Conference on Mass Spectrometry and Allied Topics, Jun. 1-5, 1997, Palm Springs, CA.

Shvartsburg, et al., "FAIMS Operation for Realistic Gas Flow Profile and Asymmetric Waveforms Including Electronic Noise and Ripple", Journal of American Society for Mass Spectrometry, 2005, pp. 1447-1455, vol. 16, Elsevier, Inc.

Shvartsburg, et al. "Optimization of the Design and Operation of FAIMS Analyzers", Journal of American Society for Mass Spectrometry, 2004, pp. 2-12, vol. 16, Elsevier, Inc.

Srebalus, et al., "Gas-Phase Separations of Electrosprayed Peptide Libraries", Analytical Chemistry, Sep. 15, 1999, pp. 3918-3927, vol. 71, No. 18.

Taraszka, et al., "Mapping the Proteome of Drosophila melanogaster: Analysis of Embryos and Adult Heads by LC—IMS—MS Methods", Journal of Proteome Research, Analytical Chemistry, 2005, pp. 1223-1237, vol. 4.

Wong, et al., "Evaluation of Ion Mobility Spectroscopy for Determining Charge-Solvated versus Salt-Bridge Structures of Protonated Trimers", Journal of American Society for Mass Spectrometry, 2005, pp. 1009-1019, vol. 16, Elsevier, Inc.

\* cited by examiner

APPARATUS AND METHOD FOR FIELD ASYMMETRIC ION MOBILITY SPECTROMETRY COMBINED WITH MASS SPECTROMETRY

BACKGROUND

The present invention generally relates to an improved method and apparatus for the analysis of gas phase ions by field asymmetric ion mobility spectrometry and by mass spectrometry. Mass spectrometry is an important tool in the analysis of a wide range of chemical compounds. Specifically, mass spectrometers can be used to determine the molecular weight of sample compounds. The analysis of samples by mass spectrometry consists of three main steps: formation of gas phase ions from sample material, mass analysis of the ions to separate the ions from one another according to ion mass, and detection of the ions. A variety of means and methods exist in the field of mass spectrometry to perform each of these three functions. The particular combination of the means and methods used in a given mass spectrometer determine the characteristics of that instrument.

To mass analyze ions, for example, one might use magnetic (B) or electrostatic (E) analysis, wherein ions passing through a magnetic or electrostatic field will follow a curved path. In a magnetic field, the curvature of the path will be indicative of the momentum-to-charge ratio of the ion. In an electrostatic field, the curvature of the path will be indicative of the energy-to-charge ratio of the ion. If magnetic and electrostatic analyzers are used consecutively, then both the momentum-to-charge and energy-to-charge ratios of the ions will be known and the mass of the ion will thereby be determined. Other well known mass analyzers are the quadrupole (Q), the ion cyclotron resonance (ICR), the time-of-flight (TOF), and the Paul ion trap analyzers. More recently, linear quadrupole ion traps (as described in J. Schwartz, M. Senko, and J. Syka, *J. Am. Soc. Mass Spectrom.* 13, 659(2002); J. Hager, *Rapid Commun. Mass Spectrom.* 16, 512(2002)) have become more widespread. Also, a new analyzer, the "orbitrap", based on the Kingdon trap (as described in K. Kingdon, *Phys. Rev.* 21, 408(1923)) was recently described by A. Makarov (Q. Hu et al., *J Mass Spectrom.* 40, 430(2005)). The analyzer used in conjunction with the apparatus and method described herein may be any of a variety of these.

Before mass analysis can begin, gas phase ions must be formed from a sample material. If the sample material is sufficiently volatile, ions may be formed by electron ionization (EI) or chemical ionization (CI) of the gas phase sample molecules. Alternatively, for solid samples (e.g., semiconductors, or crystallized materials), ions can be formed by desorption and ionization of sample molecules by bombardment with high energy particles. Further, Secondary Ion Mass Spectrometry (SIMS), for example, uses keV ions to desorb and ionize sample material. In the SIMS process a large amount of energy is deposited in the analyte molecules, resulting in the fragmentation of fragile molecules. This fragmentation is undesirable in that information regarding the original composition of the sample (e.g., the molecular weight of sample molecules) will be lost.

For more labile, fragile molecules, other ionization methods now exist. The plasma desorption (PD) technique was introduced by Macfarlane et al. (R. D. Macfarlane, R. P. Skowronski, D. F. Torgerson, *Biochem. Biophys. Res Commoun.* 60 (1974) 616)("McFarlane"). Macfarlane discovered that the impact of high energy (MeV) ions on a surface, like SIMS, would cause desorption and ionization of small analyte molecules. However, unlike SIMS, the PD process also results in the desorption of larger, more labile species (e.g., insulin and other protein molecules).

Additionally, lasers have been used in a similar manner to induce desorption of biological or other labile molecules. See, for example, Cotter et al. (R. B. VanBreeman, M. Snow, R. J. Cotter, *Int. J. Mass Spectrom. Ion Phys.* 49 (1983) 35; Tabet, J. C.; Cotter, R. J., Tabet, J. C., *Anal. Chem.* 56 (1984) 1662; or R. J. Cotter, P. Demirev, I. Lys, J. K. Olthoff, J. K.; Lys, I.: Demirev, P.: Cotter et al., R. J., *Anal. Instrument.* 16 (1987) 93). Cotter modified a CVC 2000 time-of-flight mass spectrometer for infrared laser desorption of non-volatile biomolecules, using a Tachisto (Needham, Mass.) model 215G pulsed carbon dioxide laser. The plasma or laser desorption and ionization of labile molecules relies on the deposition of little or no energy in the analyte molecules of interest.

The use of lasers to desorb and ionize labile molecules intact was enhanced by the introduction of matrix assisted laser desorption ionization (MALDI) (as described in K. Tanaka, H. Waki, Y. Ido, S. Akita, Y. Yoshida, T. Yoshica, *Rapid Commun. Mass Spectrom.* 2 (1988) 151 and M. Karas, F. Hillenkamp, *Anal. Chem.* 60 (1988) 2299). In the MALDI process, an analyte is dissolved in a solid, organic matrix. Laser light of a wavelength that is absorbed by the solid matrix but not by the analyte is used to excite the sample. Thus, the matrix is excited directly by the laser, and the excited matrix sublimes into the gas phase carrying with it the analyte molecules. The analyte molecules are then ionized by proton, electron, or cation transfer from the matrix molecules to the analyte molecules. This process (i.e., MALDI) is typically used in conjunction with time-of-flight mass spectrometry (TOFMS) and can be used to measure the molecular weights of proteins in excess of 100,000 Daltons.

Atmospheric Pressure Ionization (API) includes a number of ion production means and methods. Typically, analyte ions are produced from liquid solution at atmospheric pressure. One of the more widely used methods, known as electrospray ionization (ESI), was first suggested for use with mass spectrometry by Dole et at. (M. Dole, L. L. Mack, R. L. Hines, R. C. Mobley, L. D. Ferguson, M. B. Alice, *J. Chem. Phys.* 49, 2240, 1968). In the electrospray technique, analyte is dissolved in a liquid solution and sprayed from a needle. The spray is induced by the application of a potential difference between the needle and a counter electrode. The spray results in the formation of fine, charged droplets of solution containing analyte molecules. In the gas phase, the solvent evaporates leaving behind charged, gas phase, analyte ions. This method allows for very large ions to be formed. Ions as large as 1 MDa have been detected by ESI in conjunction with mass spectrometry (ESMS).

In addition to ESI, many other ion production methods might be used at atmospheric or elevated pressure. For example, MALDI has recently been adapted by Laiko et al. to work at atmospheric pressure (Victor Laiko and Alma Burlingame, "Atmospheric Pressure Matrix Assisted Laser Desorption", U.S. Pat. No. 5,965,884, and Atmospheric Pressure Matrix Assisted Laser Desorption Ionization, poster #1121, 4th International Symposium on Mass Spectrometry in the Health and Life Sciences, San Francisco, Aug. 25-29, 1998) and by Standing et al. at elevated pressures (Time of Flight Mass Spectrometry of Biomolecules with Orthogonal Injection+Collisional Cooling, poster #1272, 4th International Symposium on Mass Spectrometry in the Health and Life Sciences, San Francisco, Aug. 25-29, 1998; and Orthogonal Injection TOFMS *Anal. Chem.* 71(13), 452A (1999)). The benefit of adapting ion sources in this manner is that the ion optics (i.e., the electrode structure and operation) in the mass analyzer and mass spectral results obtained are largely independent of the ion production method used.

The elevated pressure MALDI source disclosed by Standing differs from what is disclosed by Laiko et al. Specifically, Laiko et al. disclose a source intended to operate at substantially atmospheric pressure. In contrast, the source disclosed by Standing et al. is intended to operate at a pressure of about 70 mtorr.

More recently, Takats et al. (as described in Z. Takats, J. M. Wiseman, B. Gologan, and R. G. Cooks, Science 306, 471 (2004)) introduced yet another atmospheric pressure ionization method known as desorption electrospray ionization (DESI). According to Takats et al., DESI is a method for producing ions from analyte on a surface. Electrosprayed charged droplets and ion of solvent are directed at the surface under study. The impact of the charged droplets on the surface results in the desorption and ionization of the analyte to form gas phase analyte ions.

Analyte ions produced via an API method need to be transported from the ionization region through regions of differing pressures and ultimately to a mass analyzer for subsequent analysis (e.g., via time-of-flight mass spectrometry (TOFMS), Fourier transform mass spectrometry (FTMS), etc.). In some prior art sources, this was accomplished through use of a small orifice between the ionization region and the vacuum region. In other prior art, dielectric capillaries have been used to transmit ions entrained in a carrier gas from a high pressure ion production region into the vacuum chamber of mass spectrometers—see, for example, Fenn et al., U.S. Pat. No. 4,542,293 and Whitehouse et al., U.S. Pat. No. 5,844,237. In U.S. Pat. No. 6,777,672, incorporated herein by reference, Park describes a multiple section capillary for interfacing various ion production means and for transporting ions into the vacuum chamber of a mass spectrometer.

Figure 1:
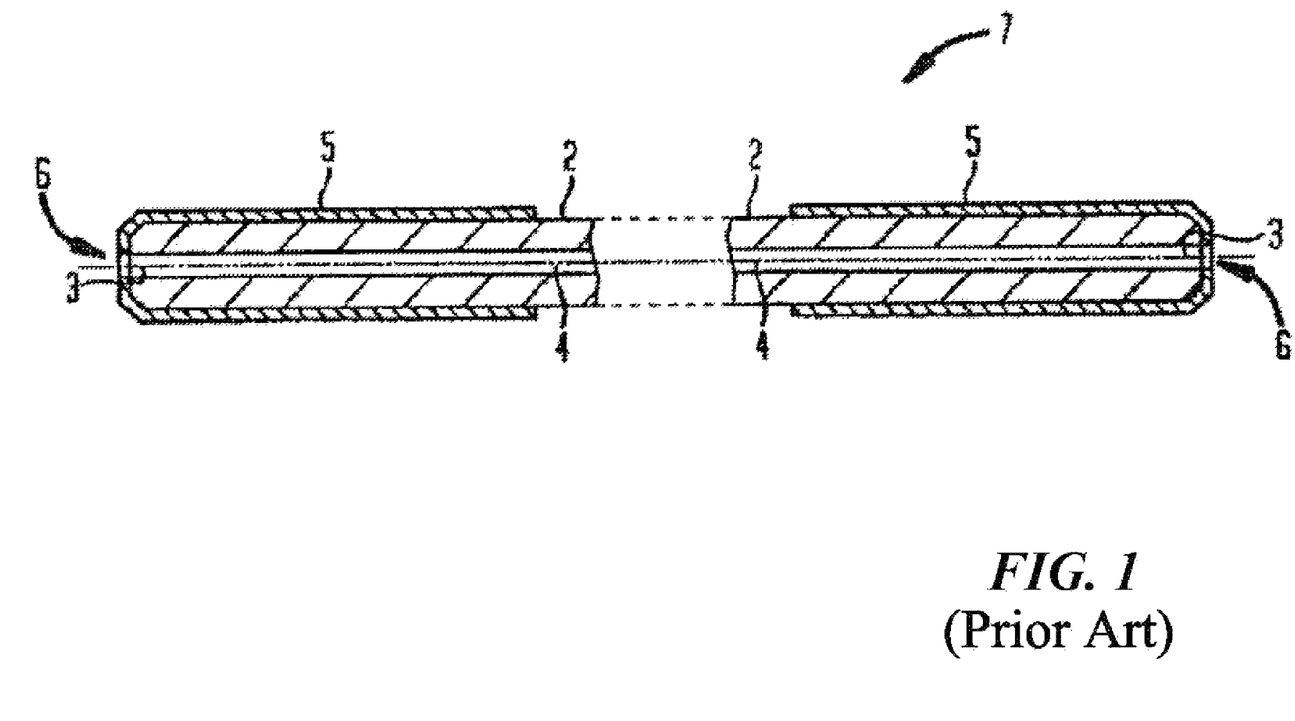
FIG. 1 shows a partial cut-away cross-sectional view of a prior art capillary comprising a unitary dielectric tube having a cylindrical outer surface and internal bore.

An example of a prior art capillary tube is shown in FIG. 1. As depicted, capillary 7 comprises a generally cylindrical glass tube 2 having an internal bore 4. The ends of capillary 7 include a metal coating (e.g., platinum, copper, etc.) to form conductors 5 which encompass the outer surface of capillary 7 at its ends, leaving a central aperture 6 such that the entrance and exit to internal bore 4 are left uncovered. Conductors 5 may be connected to electrical contacts (not shown) in order to maintain a desired space potential at each end of capillary 7. In operation, a first electrode (one of conductors 5) of capillary 7 may be maintained at an extreme negative potential (e.g. −4,500V). This first electrode 5 acts as the entrance end of the capillary and resides at near atmospheric pressure. Positively charged analyte ions formed in the atmospheric pressure ion production region are attracted to the first electrode 5 and are entrained in the gas flow into the capillary. A second electrode (the other of conductors 5), acts as the exit end of the capillary and resides at the pressure of the first vacuum region of the mass spectrometer. This second of conductors 5 may form the first stage of a multi-stage lensing system for the final direction of the ions to the spectrometer, and may be maintained at a positive potential (e.g., 160 volts).

Importantly, ions are carried through the transfer capillary by entrainment in gas which is pumped from the ion production region, through the capillary, into the first vacuum region of the mass spectrometer. Typically, the gas pressure at the capillary inlet is about one atmosphere whereas the pressure at the capillary outlet, into the first pumping region, is between one and three millibar. Under these conditions, the velocity of the gas in the capillary is about 100 m/s. It is the "force" associated with this high velocity gas that is able to drive the ions away from the electrically attractive potential at the capillary entrance and towards the electrically repulsive potential at the capillary exit.

Figure 2:
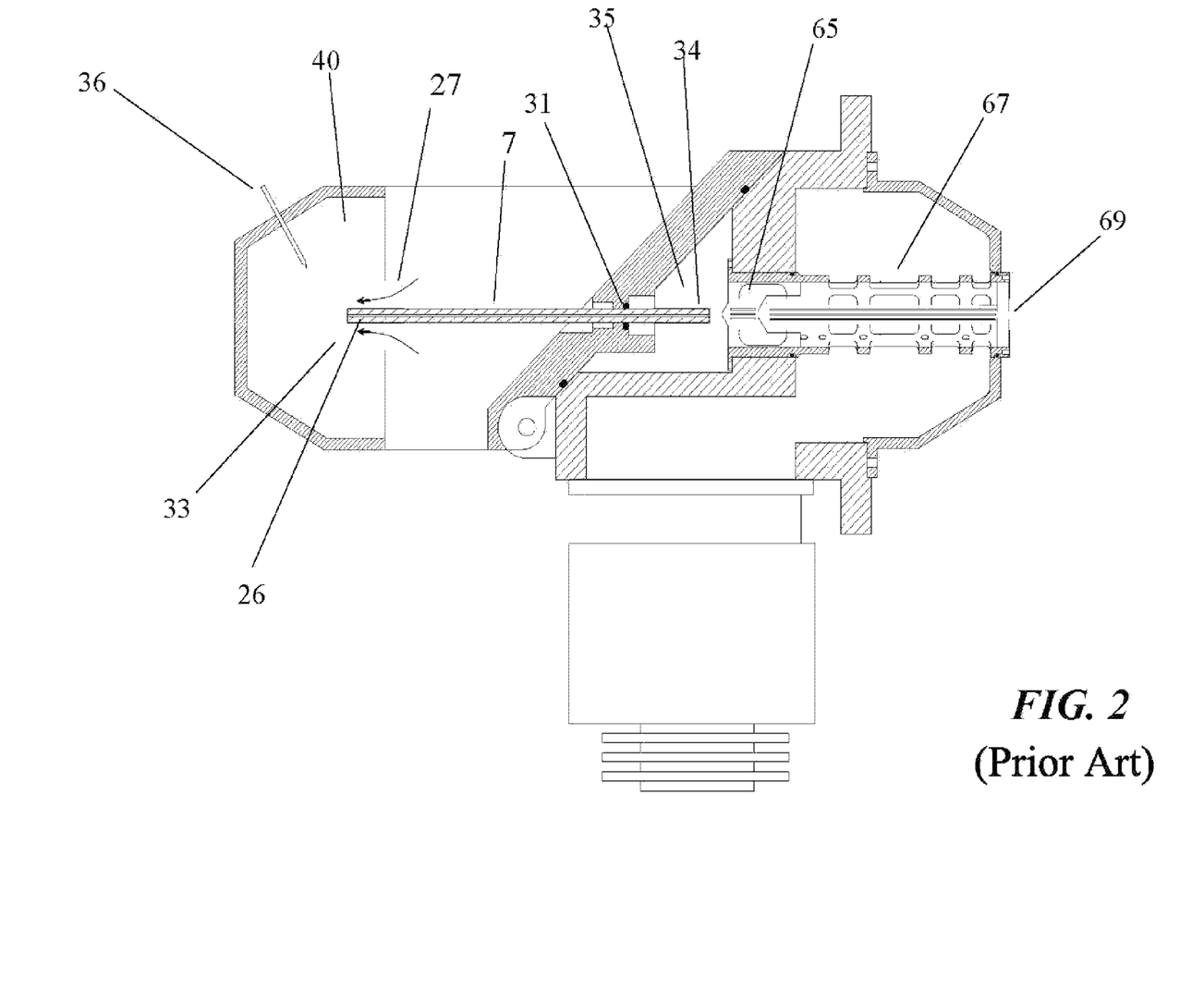
FIG. 2 is a depiction of a prior art API ion source including an ion transfer capillary.

FIG. 2 depicts prior art capillary 7 as incorporated in a prior art ion source. Capillary 7 extends from ion production region 40, into first vacuum region 35 of the ion source. O-ring 31 forms a seal between capillary 7 and the wall of vacuum region 35. Entrance end 26 of capillary 7 is substantially covered by apertured endcap electrode 33. Endcap 33 is composed of a chemically resistant, electrically conducting material such as stainless steel. When producing positive analyte ions, endcap 33 may be held at a potential of −4 kV and capillary entrance 26 may be held at a potential of −4.5 kV. Solution containing analyte is nebulized via sprayer 36. Sprayer 36 is held at near ground potential. As a result of the potential difference between sprayer 36 and endcap 33, the droplets formed via sprayer 36 are positively charged. Drying gas 27 is introduced into region 40 via the aperture in endcap 33. Solvent in the droplets formed via sprayer 36 evaporates into drying gas 27. Drying gas 27 may be heated to accelerate solvent evaporation. The complete, or near complete, evaporation of solvent from the analyte droplets results in gas phase analyte ions. The analyte ions are attracted by the electric field and by gas flow into aperture 6 (FIG. 1) of capillary 7. Solvent is substantially removed from the flow of ions into aperture 6 by the flow of drying gas 27 counter to the flow of the ions. Because the solvent molecules resulting from the evaporation of analyte droplets are electrically neutral, they are not as attracted towards aperture 6 as are the analyte ions. The counter current flow of drying gas 27 therefore tends to carry the solvent molecules away from aperture 6.

Once through capillary 7, the analyte ions are guided by a combination of gas flows and electric fields through differential pumping regions 65 and 67 to the outlet 69 of the ion source. On exiting the source through outlet 69, the ions either directly or indirectly enter the mass analyzer (not shown). In the mass analyzer the ions are mass analyzed and detected so as to yield a mass spectrum. Any known mass analyzer or combination of mass analyzers including time-of-flight, quadrupole, Paul trap, linear ion trap, orbitrap, electric or magnetic sector, or ion cyclotron resonance analyzers might be used.

Ion mobility spectrometry (IMS) is a method whereby the "mobility" of analyte ions through a gas is measured under the influence of a static electric field. IMS is described in detail in the literature [see, for example, G. Eiceman and Z. Karpas, Ion Mobility Spectrometry (CRC. Boca Raton, Fla. 1994); and Plasma Chromatography, edited by T. W. Carr (Plenum, New York, 1984)]. At low electric field strengths—e.g. a few kilovolts per cm—the speed of analyte ions through a gas is measured. To start the measurement, ions are pulsed into the entrance of the mobility analyzer. In the mobility analyzer, a uniform electric field accelerates the ions towards the end of the analyzer. Collisions with gas in the analyzer tends to dampen the ion motion. The action of the electric field and collision of ions with the gas thus results in an average ion speed through the gas. At the far end of the analyzer, the ions strike a detector and are detected. By measuring the time between the introduction of ions into the analyzer and the detection of the ions, the speed of the ions, and therefore their mobility can be determined.

At low field strengths, the mobility of an ion is a constant relating the speed of the ion to the strength of the electric field. However, at high electric field strengths, the mobility of the ions varies with electric field strength. This gives rise to field asymmetric ion mobility spectrometry (FAIMS)—an extension of IMS which takes advantage of the change in ion mobility at high field strengths.

FAIMS is based on an observation of Mason and McDaniel [.W. McDaniel and Edward A. Mason, The mobility and diffusion of ions in gases, John Wiley & Sons, 1973] who found that the mobility of an ion varies with the applied electric field strength. Above an electric field to gas density ratio (E/N) of 40 Td (E>10,700 V/cm at atmospheric pressure) the mobility coefficient K(E) has a non-linear dependence on the field. This dependence is believed to be specific for each ion species. A coefficient "$\alpha$" describes the change in mobility as a function of field strength and is defined as the fractional change in mobility when comparing a high field strength condition to a low field strength condition. An $\alpha$ value of 0.1, for example, represents an increase of 10% in the ion's mobility whereas an $\alpha$ value of −0.1 represents a decrease of 10% in the ion's mobility.

FAIMS is described in detail in the literature [I. Buryakov, E. Krylov, E. Nazarov, and U. Rasulev, Int. J. Mass Spectrom. Ion Phys. 128. 143 (1993); D. Riegner, C. Harden, B. Carnahan, and S. Day, Proceedings of the 45th ASMS Conference on Mass Spectrometry and Allied Topics, Palm Springs, Calif., Jun. 1-4, 1997, p. 473; B. Carnahan, S. Day, V. Kouznetsov, M. Matyjaszczyk, and A. Tarassov Proceedings of the 41st ISA Analysis Division Symposium, Framingham, Mass., Apr. 21-24, 1996, p. 85; and B. Carnahan and A. Tarassov, U.S. Pat. No. 5,420,424]. FAIMS devices measure the difference in the mobility of an ion at high field strength relative to its mobility at low field strength. That is, the ions are separated on the basis of the compound dependent behaviour of mobility as a function of electric field strength. In the prior art FAIMS devices such as described in U.S. Pat. No. 6,972,407, herein incorporated by reference, two parallel, planar conducting electrodes are used to generate an electric field in which analyte ions are to be analyzed. The analyte ions are entrained in a carrier gas which moves at high velocity (several meters per second) perpendicular to the electric field—i.e. parallel to the surface of the planar conducting electrodes. Applying the appropriate potentials to the "top" and "bottom" electrodes will result in the filtering of ions on the basis of their $\alpha$ value. As described in the prior art literature, a rectangular waveform having repeatedly a high potential and then a low potential is applied between the electrodes. For a relatively short period of time, a high potential is applied between the electrodes and then for a longer period of time a relatively low potential of opposite polarity is applied. The magnitude of the potentials and the duration of their application are such that the time averaged potential difference is zero. During the application of the high potential ions will drift laterally with a mobility $K(1+\alpha)$. During the application of the low potential of opposing polarity, the ions will drift laterally with a mobility K and in the opposite direction to that when the high potential was applied. Applying an additional DC "compensation voltage" between the electrodes allows the selection of ions of a given mobility difference to be transmitted.

In recent years, IMS and FAIMS spectrometers have been combined with mass spectrometry. In U.S. Pat. No. 5,905,258 Clemmer and Reilly combine IMS with a time of flight mass spectrometer (TOFMS). This provided for a first analysis of the ions by IMS followed by a second analysis via TOFMS. Ultimately, this yields a two dimensional plot containing both the mobility and mass of the ions under investigation. The advantages of this type of combined analyzer over a mass spectrometer alone are described in detail in the literature [C. S. Srebalus et al., *Anal. Chem.* 71(18), 3918(1999); J. A. Taraszka et al., *J. Proteom. Res.* 4, 1223(2005); R. L. Wong, E. R. Williams, A. E. Counterman, and D. Clemmer, *J. Am. Soc. Mass Spectrom.* 16, 1009(2005)] and include the separation of chemical background from analyte species for an improved signal-to-noise ratio (S/N), and the separation of ions based on compound class or charge state for easier mass spectral interpretation.

Similarly, in U.S. Pat. No. 6,504,149, for example, Guevremont et al. combine a FAIMS device with a mass spectrometer. As detailed in the literature, a combined FAIMS mass spectrometer has similar advantages as an IMS mass spectrometer [A. Shvartsburg, K. Tang, R. Smith, *J. Am. Soc. Mass Spectrom* 16, 2(2005); D. A. Barnett B. Ells, R. Guevremont, and R. W. Purves, *J. Am. Soc. Mass Spectrom.* 13, 1282 (2002)]. For example, a combined FAIMS mass spectrometer has an improved signal-to-noise ratio over a mass spectrometer alone because the FAIMS device can filter away the chemical background.

In the instrument disclosed by Guevremont, the FAIMS device is imposed between the ion production means and the inlet to the mass spectrometer. That is, a FAIMS device may be added to a preexisting mass spectrometer by moving the ion production means and placing the FAIMS apparatus between the inlet to the mass spectrometer and the ion production means. As a result, the transmission efficiency of analyte ions from the ion production means to the mass analyzer is reduced. Although the S/N in the mass spectra produced may be improved over a mass spectrometer alone, the imposition of the FAIMS device nonetheless leads to a reduced sensitivity.

Furthermore, prior art FAIMS devices have been employed as peripheral or add-on devices when used in conjunction with mass spectrometers [B. Ells et al, *Anal. Chem.* 71, 4747 (1999)]. That is, prior art FAIMS devices are not highly integrated with mass spectrometers and users or technicians must mount and demount the FAIMS device in order to run tandem FAIMS/MS or MS—only experiments respectively. That is, if a prior art FAIMS apparatus is implemented on a mass spectrometer then it must be kept in operation in order to be of any benefit. In order to observe the entire range of ions being generated by the ion production means—i.e. without filtering via FAIMS—the asymmetric waveform must be turned off. However, the presence of the FAIMS device between the ion source and the mass spectrometer—even if deactivated—would represent a loss of ion transmission efficiency and therefore a loss in sensitivity. Thus, in a practical operation, the FAIMS apparatus must be implemented between the ion production means and the inlet of the mass spectrometer when FAIMS filtering is desired and the FAIMS apparatus must be removed again when FAIMS filtering is not desired. This added complexity discourages users from adopting FAIMS in combination with mass spectrometry.

SUMMARY

In accordance with the principles of the present invention, in a tandem FAIMS/MS instrument, the FAIMS device is integrated into the mass spectrometer such that the transmission efficiency of analyte ions is improved over prior art FAIMS devices and such that the FAIMS device need not be demounted when not in use.

In one embodiment, a dielectric material having a channel through it to form a capillary-like device. Ions entrained in a gas are transported by gas flow through the channel of the capillary from an ion production region to the first vacuum region of the mass spectrometer. The device includes apertured conducting electrodes at the entrance and exit of the channel and one or more pairs of "FAIMS electrodes" along the interior walls of the device. An asymmetric waveform can be applied between the FAIMS electrodes to effect FAIMS separations. Alternatively, the FAIMS electrodes may be held at a neutral potential such that no FAIMS separation occurs. In this case ions simply travel with the gas into the first pumping region of the mass spectrometer.

In an alternate embodiment according to the present invention, a capillary-like device consists of at least two sections. The two sections are removably joined end to end in a gas tight manner. Ions entrained in a gas are transported by gas flow through the channel of the capillary from an ion production region to the first vacuum region of the mass spectrometer. The device includes apertured conducting electrodes at the entrance and exit of the channel and one or more pairs of "FAIMS electrodes" along the interior walls of the device. The one or more pairs of FAIMS electrodes may reside in one or more sections of the capillary. An asymmetric waveform can be applied between the FAIMS electrodes to effect FAIMS separations. Alternatively, the FAIMS electrodes may be held at a neutral potential such that no FAIMS separation occurs. In this case ions simply travel with the gas into the first pumping region of the mass spectrometer. This embodiment is easier to mount and demount than prior art devices.

In still another embodiment, the FAIMS electrodes are implemented in a first capillary section that is removably joined via a gas tight union with a second capillary section. When FAIMS is not in use, this first capillary section and the union are removed and the second capillary section alone is used to simply transport ions from the ion production region to the first vacuum region of the mass spectrometer.

In yet other embodiments, a serpentine, helical, or otherwise curved channel can be used in a FAIMS device. Such a curved channel allows for a longer path and therefore a longer residence time and higher FAIMS resolution in a given length device.

DETAILED DESCRIPTION

Figure 3A:
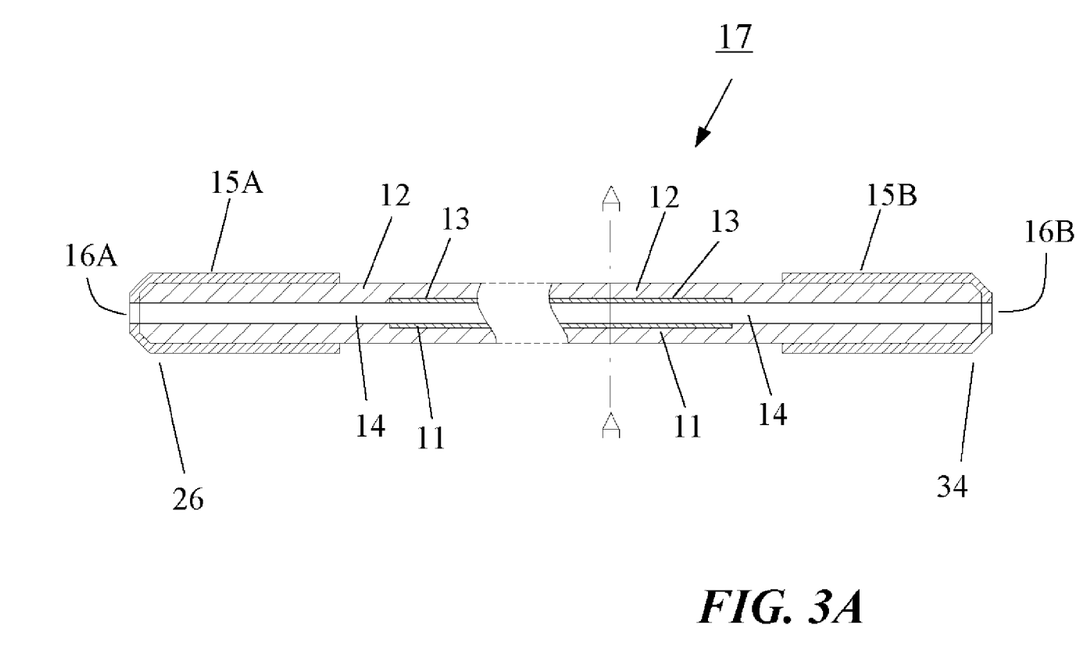
FIG. 3A is a cross sectional view of a FAIMS enabled transfer capillary according to the present invention.
Figure 3B:
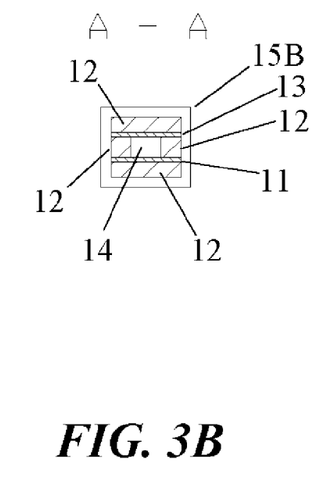
FIG. 3B is a depiction of the FAIMS enabled capillary of FIG. 3A as viewed along section A-A.

Referring to FIGS. 3A and 3B, a FAIMS device according to the present invention is depicted. As with prior art MS transfer capillaries (see FIG. 1) the device according to the present invention is designed to transport ions entrained in a gas stream from an ion production region at entrance end 26, through a channel 14, and into the vacuum system of the mass spectrometer via exit end 34. Body 12 of capillary 17 is composed of dielectric material such as glass or ceramic. Each end of capillary 17 is coated with electrically conducting layer 15A and 15B. Conductors 15A and 15B may be composed of any desired electrically conducting material—e.g. platinum or nickel. Alternatively, conductors 15A and 15B may be metal caps (as opposed to a coating). Conductors 15A and 15B have apertures 16A and 16B respectively through which gas and ions may pass.

As depicted in FIG. 3B, which is a cross-sectional diagram taken at section lines A-A, planar conducting electrodes 11 and 13 are positioned on opposite sides of channel 14 and extend laterally to the outer wall of capillary 17. Alternatively, electrodes 11 and 13 may extend laterally to the outer wall of capillary 17 only along a small portion of the capillary's length. Electrodes 11 and 13 may be composed of any electrically conducting material—e.g. steel or nickel foil—or a conducting layer deposited over an insulator—e.g. a gold coating on polyimide foil. Electrical contact with electrodes 11 and 13 is made via the conductor exposed at the surface of the outer wall.

The FAIMS device according to the present invention may have any desired dimensions. However, as an example, capillary 17 may be 300 mm long from entrance 26 to exit 34. Channel 14 may be 0.5 mm high and 1 mm wide. And electrodes 11 and 13 may extend 220 mm along channel 14 and may be 0.2 mm thick. Conductors 15A and 15B may be operated at any desired potential, however, as an example, when analyzing positive ions, entrance conductor 15A at entrance end 26 may be operated at −4,500 V and conductor 15B at exit end 34 may be held at a potential of +300 V. Similarly, any desired potential may be applied between electrodes 11 and 13. However, as an example, the applied waveform may have a period of about 5 μs. In this period, a voltage of 750 V may be applied between electrodes 11 and 13 for about 17% of the time, and a voltage of −150 V may be applied between electrodes 11 and 13 for about 83% of the time. Furthermore a DC offset—i.e. the compensation voltage (CV)—may be superimposed on the waveform. Any desired CV potential might be used, however, as an example; a CV of 10 V might be used.

Figure 4:
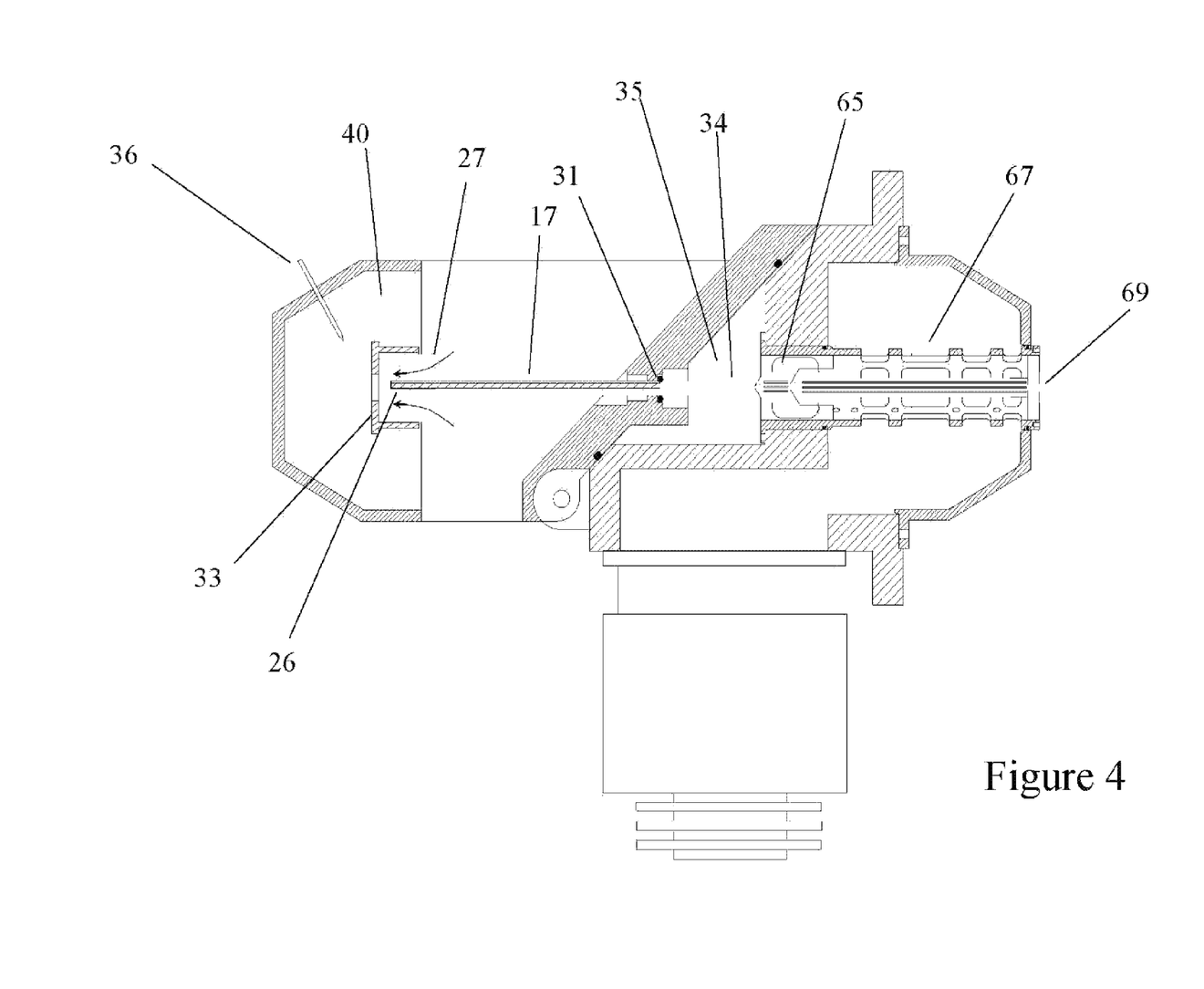
FIG. 4 is a depiction of the capillary of FIG. 3A as used in conjunction with the prior art source of FIG. 2.

Referring next to FIG. 4, in one embodiment when capillary 17 is incorporated in the ion source of a mass spectrometer, entrance end 26 will be at near atmospheric pressure whereas exit end 34 will be near one mbar during operation. As a result the speed of the carrier gas and entrained ions along channel 14 will be on the order of 100 m/s. This is several times higher than the velocity of gas in prior art FAIMS devices. However, in this embodiment, electrodes 11 and 13 are also substantially longer than in prior art FAIMS devices (e.g. 220 mm) such that ions spend approximately the same amount of time between these electrodes as they would in prior art FAIMS devices.

The resolution of FAIMS separations is directly related to the residence time of ions between the FAIMS electrodes, the period of the applied waveform, and to the speed with which the ion pass through the FAIMS device [A Shvartsburg, K. Tang, and R. Smith, J Am Soc Mass Spectrom 16, 2(2005)]. In contrast, the resolution is inversely related to the gap between the FAIMS electrodes. Because the gap between electrodes 11 and 13 is comparable to that in the prior art, because the speed of passage of the ions is greater, and because the residence time is comparable, the resolution of the FAIMS device according to the present invention is comparable to that of prior art devices.

Importantly, heated drying gas 27 can be used to desolvate droplets formed via sprayer 36 and to remove solvent molecules from the carrier gas containing the analyte ions. The removal of solvent is especially important when considering FAIMS analyses because the analyte ion will have a different mobility than the same analyte ions when adducted with solvent molecules. In prior art API ion sources, $N_2$ has been typically used as the drying gas. Nitrogen is usually preferred as a drying gas because it is chemically inert, relatively inexpensive, and easy to obtain in high purity. However, other gases have been used in special cases. The use of $SF_6$ and mixtures of $O_2$ and $N_2$ as the drying gas have been reported in the literature. Such gases are especially useful when producing negatively charged analyte ions because $SF_6$ and $O_2$ are electron scavengers and thus tend to prevent electrical discharges.

When used in conjunction with the FAIMS device of the present invention—i.e. capillary 17—drying gas 27 also acts as the carrier gas for the FAIMS separation. That is, the flow rate of drying gas 27 into ion production region 40 is much greater than the flow rate of gas into capillary 17 at entrance 26. Any flow rate of drying gas 27 might be used, however, as an example, the flow rate might be five liters per second. In contrast the flow rate of gas into capillary 17 is about 0.03 l/s. As a result, nearly all of drying gas 27 continues past entrance 26 into region 40. Region 40 and the region between endcap 33 and capillary entrance 26 therefore become filled with drying gas 27. Thus, the only gas that enters capillary 17 is that gas which also is used as drying gas 27. Analyte ions produced in region 40 become entrained in drying gas 27 and then enter capillary 17. While in capillary 17, between electrodes 11 and 13, drying gas 27 thus acts as the carrier gas for the FAIMS separation.

A variety of gases and mixtures of gases may be useful as drying gas 27, especially when performing a FAIMS separation according to the present invention. A variety of gases, including $N_2$, $CO_2$, and He, as well as mixtures of these and other gases have been used as the carrier gas in prior art FAIMS devices. Similarly, any or all of these gases and mixtures of gases might be used as drying gas 27 in conjunction with the present invention. Furthermore, reagent species may be introduced into the drying gas to further influence the FAIMS process.

In another embodiment, drying gas 27 is heated with a heater (not shown). Drying gas 27 may be heated to any desired temperature, however, as an example, drying gas 27 may be heated to a temperature of 150° C. In still another embodiment, capillary 17 is also heated to a predetermined temperature. Capillary 17 may be heated via the flow of heated drying gas around its exterior length. Alternatively, capillary 17 may be heated via a separate heater (not shown) that heats capillary 17 along substantially its entire length. Capillary 17 may be heated to any desired temperature, however, as an example, it may be maintained at a temperature of 150° C.

Heating capillary 17 in turn heats the gas—i.e. drying gas 27—as it is flowing through channel 14. Maintaining drying gas 27 (here acting as the carrier gas) at a controlled temperature is important to controlling the viscosity of the gas, the adduction of solvent or other molecules to the analyte ion, and the FAIMS separation conditions in general. For this purpose, the selection of the dielectric material which forms capillary body 12 is important. A dielectric material having a higher thermal conductivity—e.g. ceramic—is more advantageous than a dielectric having a low thermal conductivity—e.g. glass.

Electrodes 11 and 13 may be used to filter ions by the FAIMS method as described above and in the prior art. However, they might be operated in any desired manner. As an example, electrodes 11 and 13 may be held at a fixed potential such that ions entrained in the gas stream are not affected by the electrodes' presence. There are, thus, at least two modes of operation of the device—one in which the electrodes are held inactive such that substantially all ions pass from entrance end 26 to exit end 34, and a second in which electrodes 11 and 13 are used to filter the ions by FAIMS methods. When inactive, no potential difference is applied between electrodes 11 and 13.

Once through capillary 17, the analyte ions are guided by a combination of gas flows and electric fields through differential pumping regions 65 and 67 to the outlet 69 of the ion source. On exiting the source through outlet 69, the ions either directly or indirectly enter the mass analyzer (not shown). In the mass analyzer the ions are mass analyzed and detected so as to yield a mass spectrum. Any known mass analyzer or combination of mass analyzers including time-of-flight, quadrupole, Paul trap, orbitrap trap, linear ion trap, electric or magnetic sector, or ion cyclotron resonance analyzers might be used.

It should be recognized that the differential pumping and source optics represented in FIG. 4 are only exemplary. Any desired ion optics or differential pumping scheme might be used in combination with the present invention. Further, it should be recognized that any number of devices might be implemented between capillary exit 34 and the mass analyzer. For example, in alternate embodiments, a collision cell might be implemented between capillary exit 34 and the mass spectrometer. In such a case, one could generate fragment ions in the collision cell—e.g. by collision induced dissociation, infrared multiphoton dissociation, electron capture dissociation, or electron transfer dissociation. The fragment ions would then be analyzed by the mass analyzer to produce fragment ion spectra of the FAIMS selected ions.

In a further alternate embodiment, the above mentioned collision cell might be followed by a quadrupole mass filter and a second collision cell before the main mass analyzer. One could then perform FAIMS/MS/MS experiments with ion fragmentation between each stage of analysis. In short, any number of FAIMS and MS stages might be implemented according to the present invention.

Figure 5:
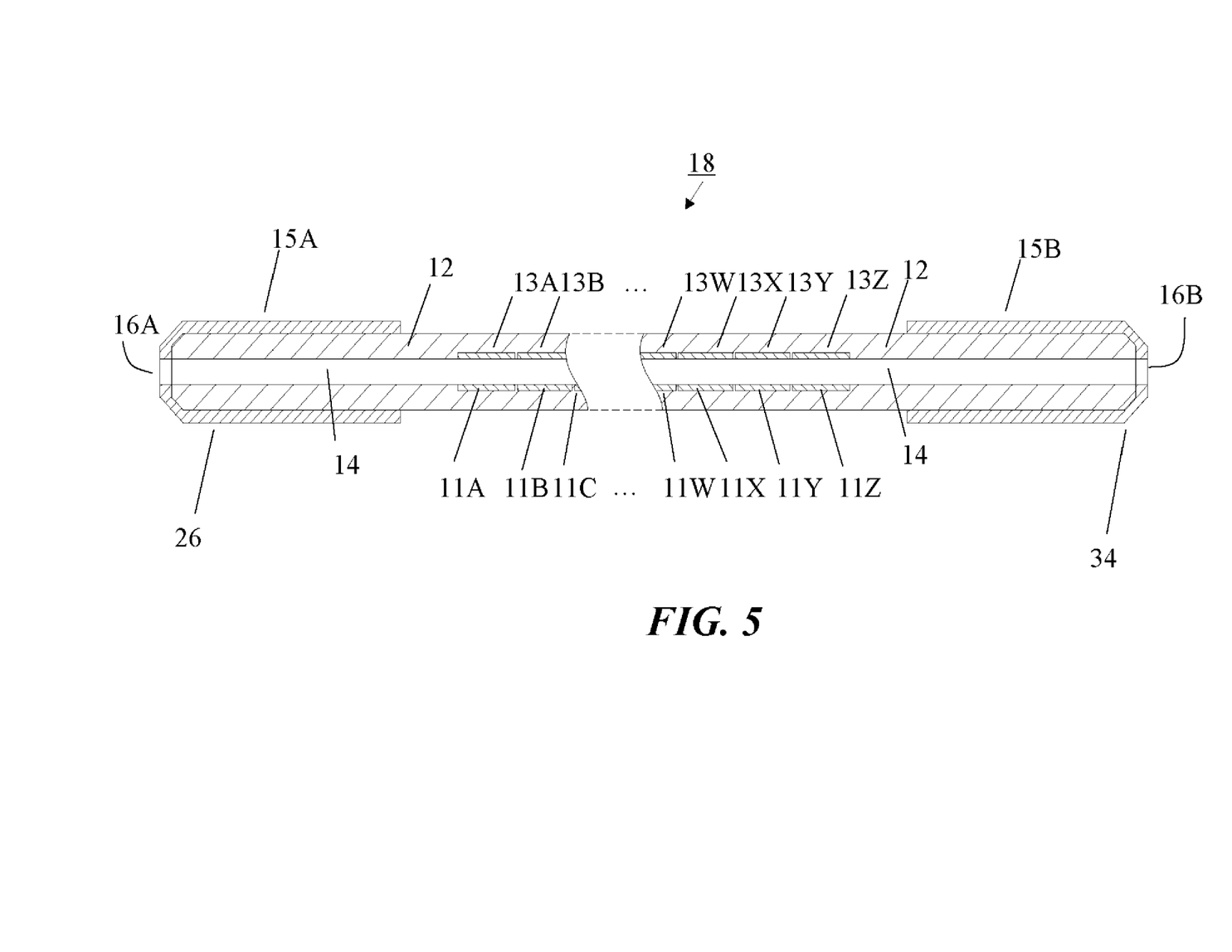
FIG. 5 is a depiction a FAIMS enabled capillary according to the present invention wherein the FAIMS electrodes are segmented at regular intervals along the capillary axis.

Referring next to FIG. 5, in another embodiment, electrodes 11 and 13 may be segmented to form a multitude of independent electrodes 11A-11Z and 13A-13Z. Any number of segments of any desired length might be used, however, as an example, 26 segments are used each 8.5 mm long. Any desired potential or waveform might be applied to these electrodes. However, as an example, some of these electrodes, for example electrodes 11W-11Z and 13W-13Z might be held at a inactive potential—i.e. no FAIMS waveform—while remaining electrodes 11A-11V and 13A-13V have the FAIMS waveform applied to them. This provides a method of electronically varying the effective length of the FAIMS electrodes without changing the physical construction of the device—i.e. capillary 18. In effect this allows the FAIMS resolution to be varied so that ions of a broader range of CV values may be transmitted simultaneously.

Alternatively, the amplitude of the FAIMS waveform might be varied as a function of position along the length of capillary 18. With reference to FAIMS the strength of the electric field is always reported as E/N where E is the field strength in volts/cm and N is the number density of the gas in molecules/cm$^3$. This number is reported in units of Tounsend (Td). The Tounsend is defined as (E/N)*10$^{17}$. The mobility of ions is reported as a function of field strength in Td. The significance of this with respect to the present invention is that the pressure of the gas—i.e. number density—in capillary 18 varies as a function of position. Closer to exit end 34, the pressure is lower. In operation, the number density may decrease by as much as 20% from entrance end 26 to exit end 34. In order to maintain a constant field strength, in Tounsend, the electric field strength must also be reduced as a function of position along the capillary. This will maintain the ion behavior, in terms of mobility, along the length of capillary 18 and thereby maintain the desired resolution and transmission properties of the device.

Figure 6:
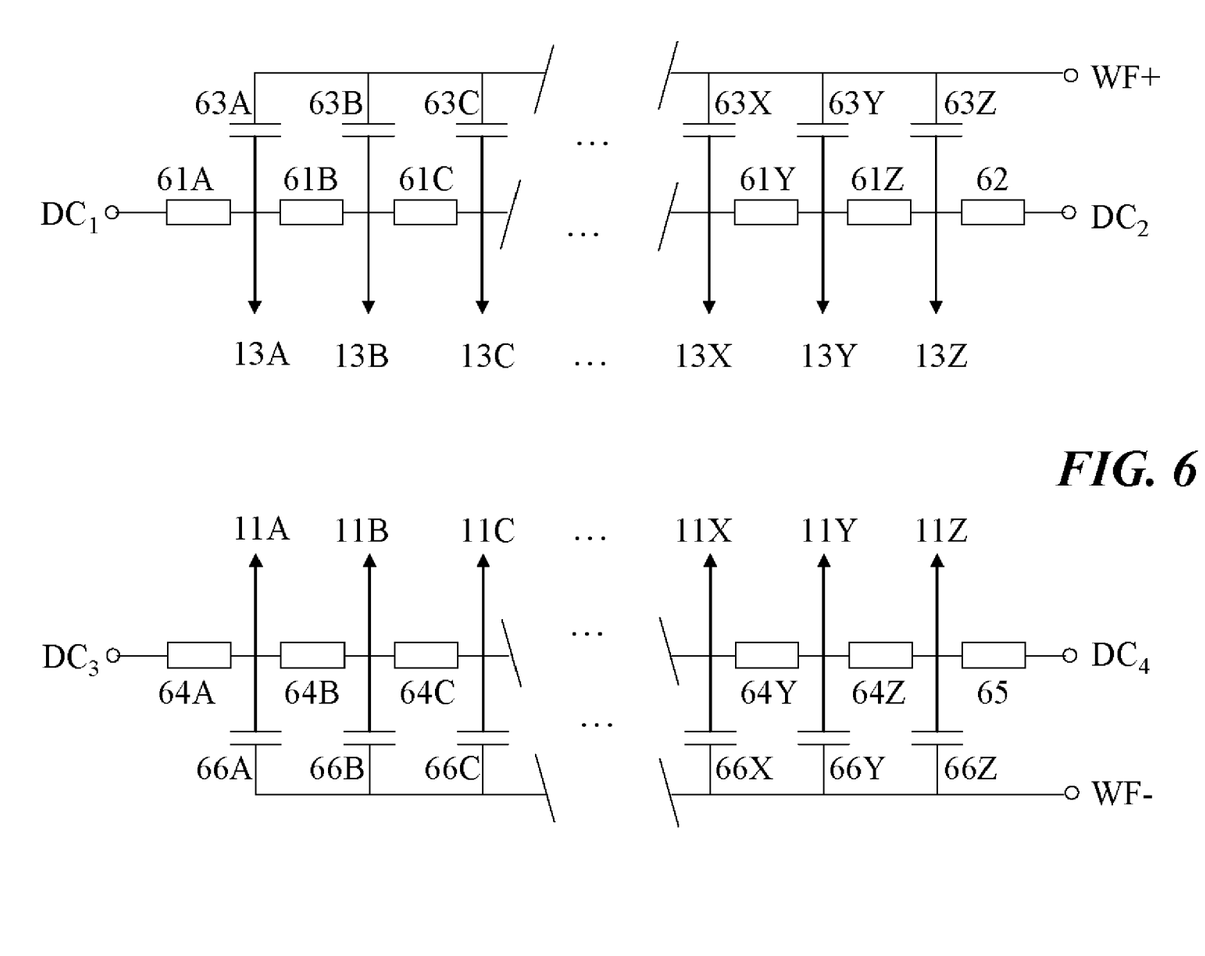
FIG. 6 is a depiction of an RC network that might be used to control electodes 11A-11Z and 13A-13Z of capillary 18 according to the present invention.

The desired waveform might be applied to electrodes 11A-11Z and 13A-13Z by any known electrical means, however, as an example, FIG. 6 depicts an RC network that might be used in conjunction with capillary 18. As shown, the RC network consists of resistors 61A-61Z, 62, 64A-64Z, and 65 as well as capacitors 63A-63Z and 66A-66Z. Resistors 61A-61Z, 62, 64A-64Z, and 65 may all have the same value. The resistors may have any desired valued, however, as an example, resistors 61A-61Z, 62, 64A-64Z, and 65 might all have a resistance of 10 Mohm. Similarly, capacitors 63A-63Z and 66A-66Z may have any desired capacitance, however, as an example, capacitors 63A and 66A may have a capacitance of 10 pF, and capacitors 63Z and 66Z may have a capacitance of 8 pF. The capacitance of remaining capacitors 63B-63Y and 66B-66Y varies linearly between 10 pF and 8 pF as a function of position within the RC network. The RC network has inputs $DC_1$ and $DC_2$ that control the DC level on electrodes 13A-13Z and $DC_3$ and $DC_4$ that control the DC level on electrodes 11A-11Z. Together inputs $DC_1$-$DC_4$ control the CV and the DC offset between electrodes 11A-11Z and 13A-13Z and between the electrodes and ground. Inputs WF+ and WF− control the AC component of the FAIMS waveform that is applied between electrodes 11A-11Z and electrodes 13A-13Z. By such an RC network, the amplitude of FAIMS waveform can varied as a function of position along capillary 18 as discussed above with respect to FIG. 5.

Figure 7A:
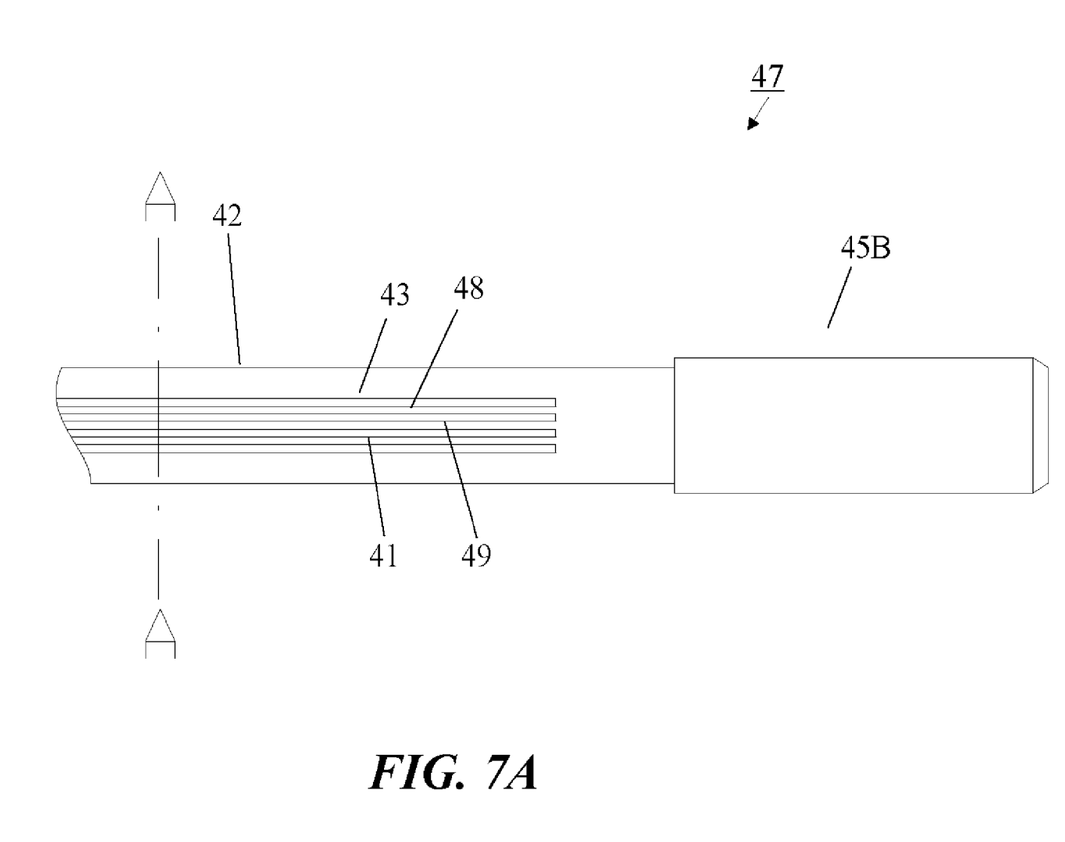
FIG. 7A is a depiction of one end of a FAIMS enabled capillary according to the present invention wherein guard electrodes are used to insure field uniformity.
Figure 7B:
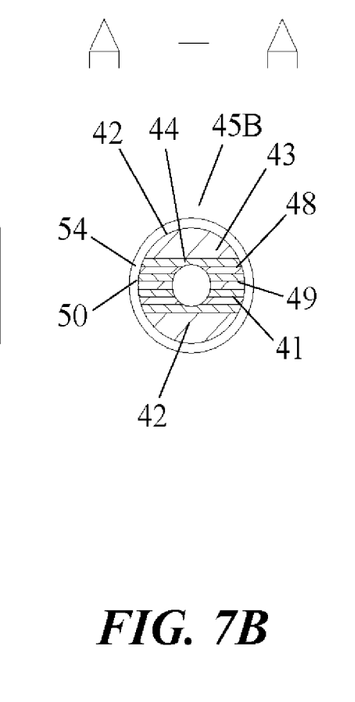
FIG. 7B is a cross sectional view of the capillary of FIG. 7A taken at line A-A.

Referring next to FIGS. 7A and 7B, shown are two views of an alternate embodiment capillary 47 according to the present invention wherein additional "guard" electrodes 48, 49, 50, and 54 are introduced between FAIMS electrodes 41 and 43. FIG. 7A is a side view of capillary 47 and FIG. 7B is a cross sectional view taken at line A-A. FAIMS electrodes 41 and 43 are formed and operated in a manner substantially the same as described with respect to FAIMS electrodes 11 and 13 above. Guard electrodes 48, 49, 50, and 54 are introduced between electrodes 41 and 43 in order to better insure the uniformity of the electric field in capillary channel 44.

Referring to FIG. 3, body 12 of capillary 17 being composed of dielectric material has an undefined—or at least poorly defined potential. Ions in the gas stream in channel 14 may possibly diffuse to the inner wall of the channel. If the ions diffuse to a wall defined by electrode 11 or 13 the ions will collide with the electrode and be discharged. However, if the ions diffuse to a wall of channel 14 defined by the dielectric of body 12, the charge of the ions may remain on the wall. In this way, the inner wall may charge up and thereby change its potential. It is in part for this reason that the width of channel 14 is greater than its height.

In FIGS. 7A and 7B, by introducing guard electrodes 48, 49, 50, and 54 in capillary 47, effects such as the electrical charging of the inner wall can be substantially reduced. In the embodiment of the present invention as represented by capillary 47, the dielectric material forming body 42 has a much reduced influence on the FAIMS separation of the ions in channel 44. Notice in capillary 47, because guard electrodes 48, 49, 50, and 54 better define the electric field, it is possible for channel 44 to be round instead of rectangular in shape.

In the embodiment of FIG. 7, guard electrodes 48, 49, 50, and 54 may be formed from electrically conducting material—e.g. steel, Ni, Au, Pt—or may be formed by coating an insulating material with an electrical conductor. As depicted in FIG. 7B, some portion of guard electrodes 48, 49, 50, and 54 is accessible on the outer wall of capillary 47 for the purpose of forming an electrical connection. The components of capillary 47 may have any desired dimensions, however, as an example, electrodes 41, 43, 48, 49, 50, and 54 may be 0.2 mm thick with a 0.2 mm gap between these electrodes. The gap between adjacent electrodes is filled with the same dielectric material as used to make up the rest of body 42. Channel 44 may have a diameter of 1 mm and capillary 47 may have an outer diameter of 6.5 mm.

Electrodes 48 and 54 are electrically connected to one another. Similarly, electrodes 49 and 50 are electrically connected. That is, they are held at the same potential. Any desired set of potentials may be applied to electrodes 48, 54, 49, and 50, however, in the preferred embodiment, these electrodes have potentials between those applied to electrodes 43 and 41 such that a substantially uniform electric potential gradient is formed in channel 44. As an example, the potentials on electrodes 43 and 41 may be 200 V and −200 V respectively. The potential applied to electrodes 48 and 54 would then be 100 V and the potential applied to electrodes 49 and 50 would be −100 V.

Figure 8:
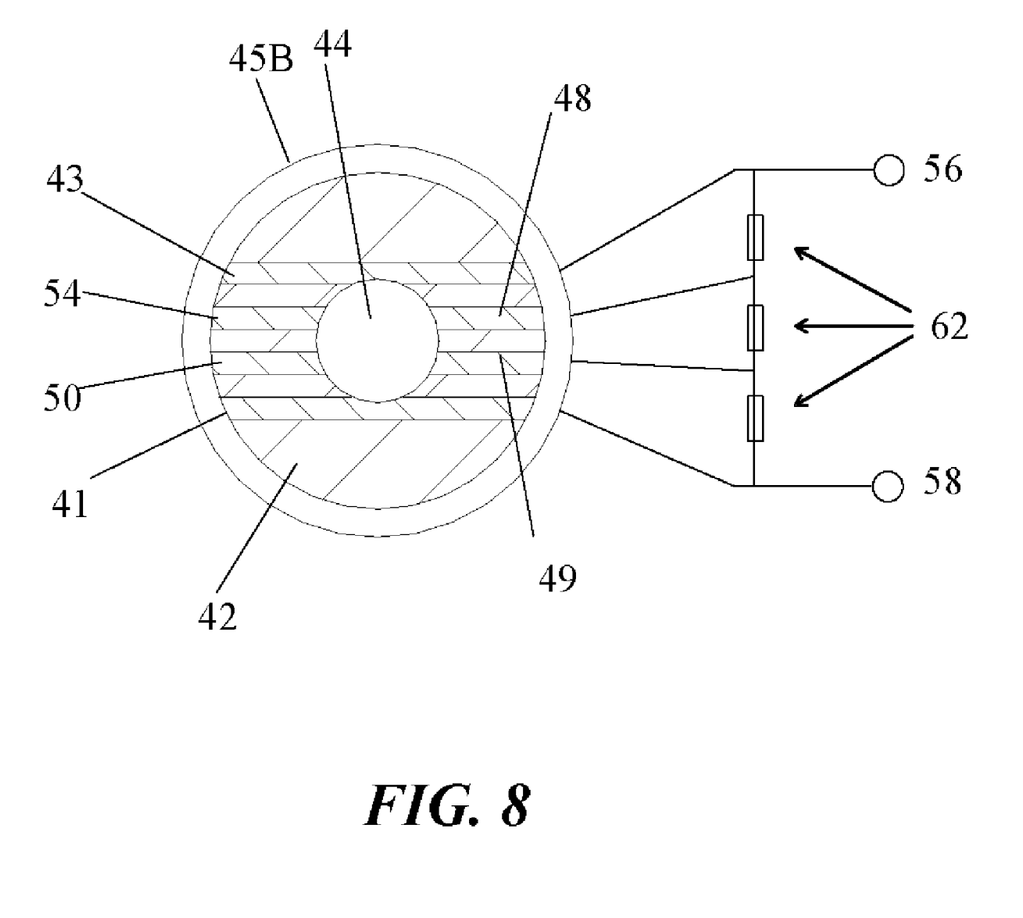
FIG. 8 depicts the electrical connection to the FAIMS electrodes of the capillary of FIG. 7A in accordance with the present invention.

The desired potentials may be applied to electrodes 43, 48, 54, 49, 50, and 41 by any known electrical means. However, as an example, FIG. 8 depicts a resistor divider that might be used in conjunction with capillary 47. In this embodiment, resistors 62 have all the same resistance. Resistors 62 could have any desired resistance, however, as an example, resistors 62 may have a resistance of 100 kohm. The potential difference that is desired between electrodes 41 and 43 is applied between inputs 58 and 56. This potential difference is divided via resistors 62 and the proper potential it thereby applied also to electrodes 48, 49, 50, and 54.

In an alternate embodiment, electrodes 48, 49, 50, and 54 may be eliminated from capillary 47. Instead, the material composing body 42 between electrodes 43 and 41 may be composed of a resistive material, for example resistive glass. The resistive material would, to a large extent, take on a potential which results in a uniform electric field in channel 44.

As described in U.S. Pat. No. 6,777,672, herein incorporated by reference, the channel in the capillaries of the present invention may be serpentine, helical, or otherwise bent. In such embodiments, the FAIMS electrodes would always appear on opposite sides of the channel, as described above. A longer channel may be particularly advantageous if it is desirable, for example, to lengthen the channel so as to increase the residence time of ions between the FAIMS electrodes and thereby improve the FAIMS resolution. By such a serpentine or helical geometry, the length of the channel can be increased without increasing the length of the capillary.

Furthermore as described in U.S. Pat. No. 6,777,672 a capillary may consist of two or more sections joined by a gas tight union. In alternate embodiments, the FAIMS device according to the present invention might be incorporated into a first section of capillary that can be removably joined with a second section of capillary, via the above mentioned gas tight union. In one alternate embodiment, the second section of capillary is substantially irremovably integrated into the ion source such that the outlet of second capillary section is in the first vacuum region of the mass spectrometer. When FAIMS separations are desired, the first capillary section, containing also the FAIMS electrodes, is joined via a union with the second capillary section. If FAIMS separations are not desired, the first capillary section is simply left away.

Figure 9:
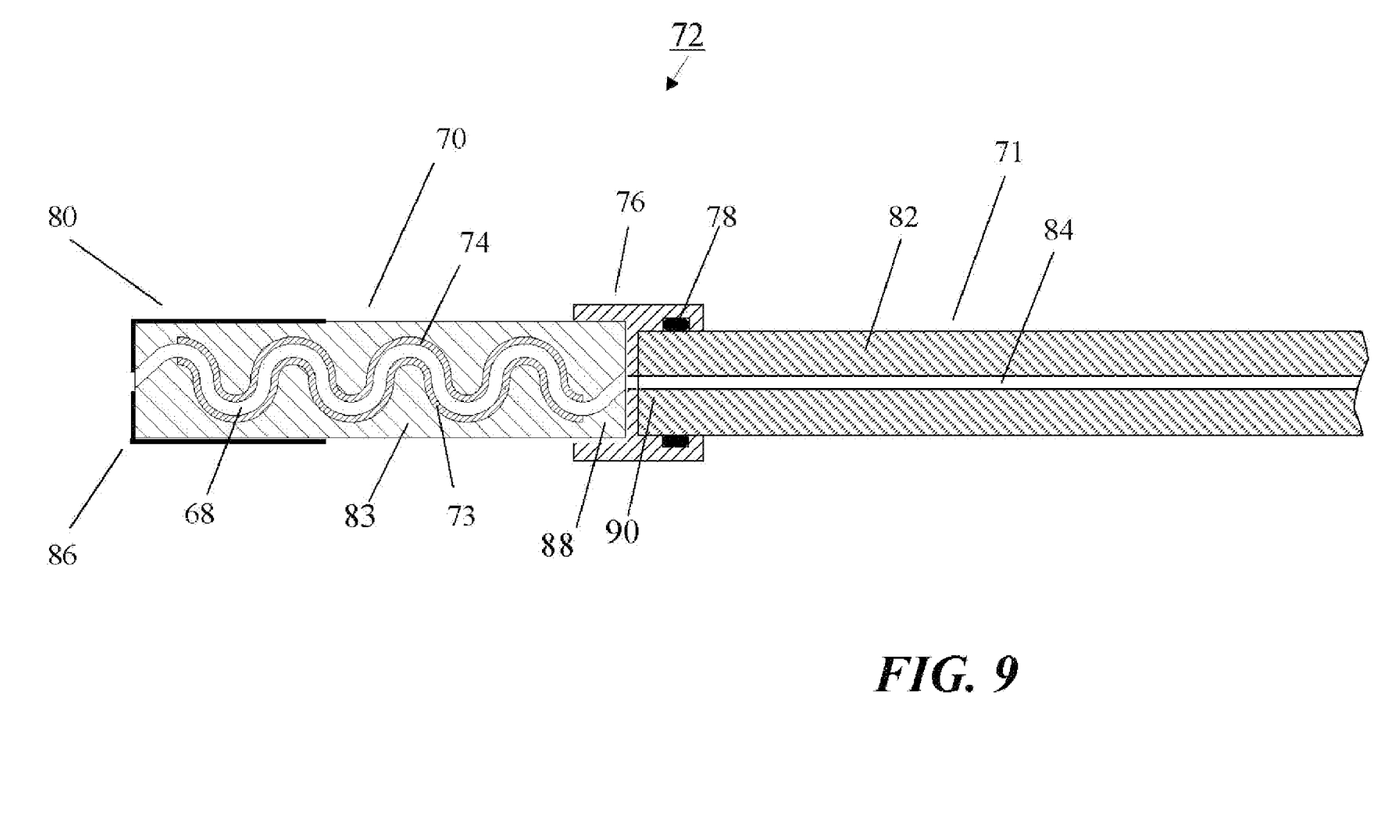
FIG. 9 depicts a multiple section capillary with incorporated FAIMS electrodes according to the present invention.

Referring next to FIG. 9, shown is an alternate embodiment device according to the present invention wherein multiple part capillary 72 consists of two capillary sections 70 and 71. While the construction may vary widely, in this specific embodiment, section 71 has dimensions and general construction similar to prior art capillary 7. Section 71 has a body 82 constructed primarily of a dielectric—i.e. glass, ceramic, etc.—and a central bore 84 through which gas and ions may pass. The outer surface and inner bore of section 71 are both substantially cylindrical. In operation, section 71 is fixed in the source of a mass spectrometer in a manner similar to that described above with respect to FIG. 2. That is, entrance end 90 of section 71 is fixed in an ion production region at near atmospheric pressure whereas the exit end of section 71 (not shown) is fixed in the first pumping region of the mass spectrometer. Capillary section 71 might have a wide variety of diameters and lengths, however, as an example, the inner and outer diameters of section 71 might be 0.6 and 6.5 mm respectively and the length of section 71 might be 180 mm.

Capillary section 70 also has a body 83 formed from dielectric material, however, channel 68 of section 70 follows a serpentine path. A wide variety of dimensions may be chosen for the serpentine path, however, as an example, the path can be described as a series of opposing semi-circles having an inner radius of 3 mm. A wide variety of dimensions may be chosen for channel 68, however, as an example, channel 68 may be 0.5 mm high—i.e. in the plane of the page—and 1 mm wide—i.e. perpendicular to the page. FAIMS electrodes 73 and 74 are positioned on either side of channel 68. FAIMS electrodes 73 and 74 may be composed of any electrically conducting material and may be of any desired thickness. However, as an example, FAIMS electrodes 73 and 74 are 0.2 mm thick.

In an alternate embodiment, the FAIMS electrodes may be planar conducting electrodes—i.e. rather than curved electrodes following the serpentine path. In such an alternate embodiment the FAIMS electrodes would be positioned on opposite sides of channel 68 but would be normal to the axes of the curve in the serpentine path—i.e. they would be parallel to the plane of the drawing in FIG. 9 and would be above and below the plane of the page.

Capillary section 70 may have any desired length and diameter, however, as an example, section 70 may have a length of 50 mm and an outer diameter of 8 mm. Entrance end 86 of section 70 includes an apertured conducting coating 80. Coating 80 may be composed of any electrically conducting material—e.g. Pt, Ni, etc. Exit end 88 of section 70 may be fixed in union 76 by, for example, epoxy. Union 76 includes an o-ring 78 such that union 76 together with section 70 may be removably joined with capillary section 71. As discussed above, when FAIMS filtering of analyte ions is desired, section 70 together with union 76 are joined with section 71. In operation, a FAIMS waveform is applied between electrodes 73 and 74 as described above. When FAIMS is not desired, section 70 and union 76 are left away and only section 71 is used to transmit ions into the mass spectrometer's vacuum system.

In an alternate embodiment, capillary channel 68 may follow a helical path. In such a case, a first FAIMS electrode may be a cylinder shaped electrode positioned on the interior of the helical path whereas the other of the FAIMS electrodes may be a cylinder shaped electrode positioned around the exterior of the helical path.

In alternate embodiments, a multitude of capillary sections—i.e. any desired number of sections more than one—might be used. In further alternate embodiments independent FAIMS electrodes may be incorporated into more than one of the capillary sections. In yet further alternate embodiments, independent FAIMS electrodes may be used to perform tandem FAIMS experiments.

Furthermore, it should be clear that any of the FAIMS devices described above in reference to the present invention may be used independent of a mass spectrometer. Detection of ions that have passed through the FAIMS device also need not occur via a mass spectrometer. Any charge or ion detection method including a channeltron, a Faraday cup or other current measurement device, or a discrete dynode multiplier, might be used.

While the invention has been shown and described with reference to a number of embodiments thereof, it will be recognized by those skilled in the art that various changes in form and detail may be made herein without departing from the spirit and scope of the invention as defined by the appended claims. Techniques, systems and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

What is claimed is:

1. Apparatus for analyzing a sample by field asymmetric ion mobility spectrometry in combination with mass spectrometry comprising:
    a capillary with a channel therethrough having an inner surface and extending from an ion production region at a first pressure to a second pressure region within a mass spectrometer so that gas flows in a direction between the ion production region and the second pressure region;
    at least one pair of electrodes positioned on opposite sides of the channel and composing at least part of the inner surface; and
    electronics for applying an asymmetric AC FAIMS waveform between said electrodes to create an electric field in a direction perpendicular to the gas flow direction that analyses the sample.

2. The apparatus of claim 1 wherein a difference in pressure between the first pressure and the second pressure is greater than 0.1 atmospheres.

3. The apparatus of claim 1 wherein the difference in pressure between the first pressure and the second pressure is greater than 0.5 atmospheres.

4. The apparatus of claim 1 further comprising means for heating the capillary.

5. The apparatus of claim 1 further comprising an ion production means located in the ion production region and selected from the group consisting of electrospray ionization, atmospheric pressure chemical ionization, matrix assisted laser desorption ionization and desorption electrospray ionization.

6. The apparatus of claim 1 wherein the mass spectrometer includes a mass analyzer selected from the group consisting of time of flight, ion cyclotron resonance, linear ion trap, quadrupole, orbitrap trap, and Paul trap analyzers.

7. The apparatus of claim 1 further comprising means for introducing a counter-current drying gas in the channel.

8. The apparatus of claim 7 wherein the drying gas is selected from the group consisting of nitrogen, helium, oxygen, carbon dioxide, argon, or mixtures thereof.

9. The apparatus of claim 7 further comprising means for heating the counter current drying gas.

10. The apparatus of claim 7 wherein the drying gas also acts as a carrier gas for the transportation of ions from the ion production region to the second pressure region.

11. The apparatus of claim 10 wherein the drying gas is selected from the group consisting of nitrogen, helium, oxygen, carbon dioxide, argon, or mixtures thereof.

12. The apparatus of claim 1 wherein the channel has a length and wherein the invention further comprises a plurality of pairs of electrodes positioned along the length of said channel.

13. The apparatus of claim 1 further comprising guard electrodes positioned between said pair of electrodes.

14. The apparatus of claim 13 further comprising a body positioned between the pair of electrodes and the guard electrodes and comprised of a resistive material that divides a potential between the pair of electrodes and applies the divided potential to the guard electrodes.

15. The apparatus of claim 14 wherein the potential is divided so as to produce a substantially uniform electric field in the channel.

16. The apparatus of claim 1 wherein the channel has a rectangular cross section.

17. The apparatus of claim 1 wherein the channel has a circular cross section.

18. The apparatus of claim 1 wherein the channel follows a curved path.

19. The apparatus of claim 18 wherein the channel follows a serpentine path.

20. The apparatus of claim 18 wherein the channel follows a helical path.

21. A method for analyzing a sample by field asymmetric ion mobility spectrometry in combination with mass spectrometry comprising:
  (a) providing a capillary with a channel therethrough having an inner surface and extending from an ion production region at a first pressure to a second pressure region within a mass spectrometer so that gas flows in a direction between the ion production region and the second pressure region;
  (b) positioning at least one pair of electrodes on opposite sides of the channel and composing at least part of the inner surface; and
  (c) applying an asymmetric AC FAIMS waveform between the electrodes to create an electric field in a direction perpendicular to the gas flow direction that analyzes the sample.

* * * * *